United States Patent
Hilliard et al.

(10) Patent No.: US 10,429,276 B2
(45) Date of Patent: Oct. 1, 2019

(54) MOTORIZED TRACKING OF SAMPLE CELL WITHIN SPECIMEN CHAMBER AND METHODS OF USING THE SAME

(71) Applicant: Elemental Scientific Lasers, LLC, Omaha, NE (US)

(72) Inventors: Shane Robert Hilliard, Bozeman, MT (US); Leif Christian Summerfield, Bozeman, MT (US); Erik Barnholt Larsen, Bozeman, MT (US)

(73) Assignee: Elemental Scientific Lasers, LLC, Omaha, NE (US)

( * ) Notice: Subject to any disclaimer, the term of this patent is extended or adjusted under 35 U.S.C. 154(b) by 20 days.

(21) Appl. No.: 15/089,845

(22) Filed: Apr. 4, 2016

(65) Prior Publication Data

US 2016/0320269 A1 Nov. 3, 2016

Related U.S. Application Data

(60) Provisional application No. 62/155,312, filed on Apr. 30, 2015.

(51) Int. Cl.

| | |
|---|---|
| *G01N 1/04* | (2006.01) |
| *G01N 35/00* | (2006.01) |
| *G01N 1/44* | (2006.01) |
| *H01J 49/04* | (2006.01) |
| *G01N 30/72* | (2006.01) |
| *G01N 35/10* | (2006.01) |
| *G01N 21/71* | (2006.01) |

(52) U.S. Cl.
CPC ............... *G01N 1/04* (2013.01); *G01N 1/44* (2013.01); *G01N 30/72* (2013.01); *G01N 35/1095* (2013.01); *H01J 49/0418* (2013.01); *G01N 21/714* (2013.01); *G01N 2001/045* (2013.01)

(58) Field of Classification Search
CPC ............ G01N 1/04; G01N 1/44; G01N 30/72
See application file for complete search history.

(56) References Cited

U.S. PATENT DOCUMENTS

| | | | |
|---|---|---|---|
| 6,358,749 B1 * | 3/2002 | Orthman | .................. G01N 1/04 359/368 |
| 2002/0090122 A1 * | 7/2002 | Baer | .................... G01N 1/2813 382/128 |
| 2006/0087643 A1 * | 4/2006 | Donovan | ................. G01N 1/44 356/36 |
| 2007/0031816 A1 * | 2/2007 | Schuetze | .............. G01N 1/2813 435/4 |

(Continued)

*Primary Examiner* — Krishnan S Menon
*Assistant Examiner* — Dwan A Gerido
(74) *Attorney, Agent, or Firm* — Kevin E. West; Advent, LLP

(57) ABSTRACT

A sampling apparatus (100) employs a cell-positioning system to move a sample capture cell (138) relative to a specimen positioning system (124). The cell-positioning system may be controlled to move sample capture cell (138) opposite to movement of the specimen positioning system (124) to maintain alignment of the sample capture cell (138) with an optical path of a laser beam of a sample generator (108). Alternatively or additionally, the cell-positioning system may be controlled to move sample capture cell (138) in response to alignment deviation of a reference beam on a quadrant detector (404).

19 Claims, 5 Drawing Sheets

(56) References Cited

U.S. PATENT DOCUMENTS

| | | | |
|---|---|---|---|
| 2007/0066967 A1* | 3/2007 | Sieckmann | G01N 1/2813 606/10 |
| 2011/0252935 A1* | 10/2011 | Welsh | G01N 1/08 83/37 |
| 2014/0223991 A1 | 8/2014 | Hilliard et al. | |
| 2014/0227776 A1 | 8/2014 | Sharp et al. | |

* cited by examiner

MOTORIZED TRACKING OF SAMPLE CELL WITHIN SPECIMEN CHAMBER AND METHODS OF USING THE SAME

CROSS REFERENCE TO RELATED APPLICATION

This application is a non-provisional application of U.S. Provisional Patent Application No. 62/155,312, which was filed on Apr. 30, 2015, the contents of which are herein incorporated by reference in their entirety for all purposes.

COPYRIGHT NOTICE

© 2016 Electro Scientific Industries, Inc. A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR § 1.71(d).

TECHNICAL FIELD

This application relates to systems and methods for capturing and transporting a sample of specimen material provided from a laser ablation site on a specimen (e.g., in the form of particles and/or vapor) to a sample analysis system and, in particular, to systems and methods for controlling the position of a sample collection cell for collecting a portion of the sample.

BACKGROUND

Laser ablation inductively coupled plasma mass spectrometry (LA-ICP-MS) or laser ablation inductively coupled plasma optical emission spectrometry (LA-ICP-OES) techniques can be used to analyze the composition of a specimen (e.g., a solid or liquid specimen material). Often, a sample of the specimen is provided to an analysis system in the form of an aerosol (i.e., a suspension of solid and possibly liquid particles and/or vapor in a carrier gas, such as helium gas). The sample is typically produced by arranging the specimen within a laser ablation chamber (also referred to as a "specimen chamber"), introducing a flow of a carrier gas within the chamber, and ablating a portion of the specimen with one or more laser pulses to generate a plume containing particles and/or vapor, ejected or otherwise generated from the specimen (hereinafter referred to as "specimen material"), suspended within the carrier gas. Entrained within the flowing carrier gas, the specimen material is transported to an analysis system via a transport conduit to an inductively coupled plasma (ICP) torch where it is ionized. A plasma containing the ionized particles and/or vapor is then analyzed by an analysis system such as an mass spectrometry (MS) or optical emission spectrometry (OES) system.

As specimen chamber sizes for LA-ICP-MS and LA-ICP-OES increase, efficient collection of the specimen material becomes more desirable. A secondary volume (also referred to as a "sample cell, "sample capture cell," or "cup") is employed within the specimen chamber to localize extraction of the sample of the specimen material within the plume generated by the laser. There are two conventional methods for maintaining the secondary volume relative to a fixed location of the optical path of the laser pulses.

One method employs a noncontact magnetic coupling, through a window in the specimen chamber, between the secondary volume and a fixed reference magnet outside the specimen chamber. The secondary volume can be moved freely in two axes by means of a pair of precision bearing sliders. Flexible sample extraction tubing routes the sample from the secondary volume to the sample analysis system through a fixed location on a wall of the specimen chamber. Another method involves tracking the secondary volume relative to a fixed position by employing a fixed arm that slides through a rotatable piston seal in the wall of the specimen chamber. Both of these methods have advantages and disadvantages.

SUMMARY

This summary is provided to introduce a selection of concepts in a simplified form that are further described in greater detail below. This summary is not intended to identify key or essential inventive concepts of the claimed subject matter, nor is it intended for determining the scope of the claimed subject matter.

In some embodiments, an apparatus for handling specimen material removed from a laser ablation site of a specimen, comprises: a specimen stage configured to support the specimen; a sample capture cell configured to receive specimen material removed from the laser ablation site when the sample capture cell is operably proximate to the laser ablation site; and a cell-positioning system configured to move the sample capture cell relative to the specimen stage, the cell-positioning system including at least one actuator for imparting motion to the sample capture cell.

In some embodiments, the at least one actuator includes a mechanical actuator.

In some alternative, additional, or cumulative embodiments, the at least one actuator includes an electro-mechanical actuator.

In some alternative, additional, or cumulative embodiments, the electro-mechanical actuator may include a stepper motor, a DC motor with encoder, or the like, or any combination thereof.

In some alternative, additional, or cumulative embodiments, the at least one actuator includes a hydraulic actuator.

In some alternative, additional, or cumulative embodiments, the at least one actuator includes a pneumatic actuator.

In some alternative, additional, or cumulative embodiments, the at least one actuator includes a piezoelectric actuator.

In some alternative, additional, or cumulative embodiments, the at least one actuator includes a magnetic actuator.

In some alternative, additional, or cumulative embodiments, the cell-positioning system is coupled to the specimen stage.

In some alternative, additional, or cumulative embodiments, the cell-positioning system is coupled to the specimen chamber.

In some alternative, additional, or cumulative embodiments, the at least one actuator is coupled to the specimen stage.

In some alternative, additional, or cumulative embodiments, the cell-positioning system includes at least one cell stage coupled to the sample capture cell and configured to guide movement of the sample capture cell.

In some alternative, additional, or cumulative embodiments, the cell-positioning system includes a robotic arm having, as an end effector, the sample capture cell.

In some alternative, additional, or cumulative embodiments, the robotic arm is an articulated arm.

In some alternative, additional, or cumulative embodiments, the at least one cell stage includes a linear stage.

In some alternative, additional, or cumulative embodiments, the at least one cell stage includes a rotary stage.

In some alternative, additional, or cumulative embodiments, the cell-positioning system includes: a first cell-positioning subsystem configured to move the sample capture cell relative to the specimen stage along a first direction; and a second cell-positioning subsystem configured to move the sample capture cell relative to the specimen stage along a second direction different from the first direction.

In some alternative, additional, or cumulative embodiments, the first cell-positioning subsystem includes: a first screw gear coupled to the specimen stage and extending along the first direction; a carriage coupled to first screw gear and the sample capture cell; and a first motor coupled to the first screw gear, wherein the first motor is configured to rotate the first screw gear, wherein the carriage is coupled to the first screw gear such that rotation of the first screw gear causes relative linear motion of the carriage along the first direction.

In some alternative, additional, or cumulative embodiments, the first cell-positioning subsystem includes a linear stage.

In some alternative, additional, or cumulative embodiments, the first cell-positioning subsystem further includes a first guide coupled to the specimen stage and to the carriage assembly, and wherein the sample capture cell is located between first screw gear and the first guide.

In some alternative, additional, or cumulative embodiments, the first guide is a screw gear.

In some alternative, additional, or cumulative embodiments, the first guide is a non-threaded rod.

In some alternative, additional, or cumulative embodiments, a mechanical link couples the first guide to the first screw gear such that rotation of the first screw gear causes a corresponding rotation of the first guide.

In some alternative, additional, or cumulative embodiments, the mechanical link is a chain (e.g., a roller chain), track, or other perforated or indented material.

In some alternative, additional, or cumulative embodiments, each of the first guide and first screw gear is provided with a sprocket that engages with the mechanical link.

In some alternative, additional, or cumulative embodiments, the mechanical link is a cable or belt.

In some alternative, additional, or cumulative embodiments, each of the first guide and first screw gear is provided with a pulley that engages with the mechanical link.

In some alternative, additional, or cumulative embodiments, the mechanical link is an assembly of gears.

In some alternative, additional, or cumulative embodiments, each of the first guide and first screw gear is provided with a gear that meshes with the gear assembly.

In some alternative, additional, or cumulative embodiments, the carriage is coupled to the first guide such that rotation of the first guide causes relative linear motion of the carriage assembly along the first direction.

In some alternative, additional, or cumulative embodiments, the second cell-positioning subsystem includes: a second screw gear coupled to the carriage assembly and extending along the second direction; and a second motor coupled to the second screw gear, wherein the first motor is configured to rotate the first screw gear, wherein the carriage assembly is coupled to the first screw gear such that rotation of the first screw gear causes relative linear motion of the carriage assembly along the first direction.

In some alternative, additional, or cumulative embodiments, a method for collecting a sample from a specimen in specimen chamber that is sealed against ambient atmosphere, comprises: moving a specimen stage to move the specimen in the chamber supported by the specimen stage, wherein movement of the specimen stage causes movement of the specimen relative to an optical path of a sample generator; moving a sample capture cell to maintain a capture position relative to the optical path of the sample generator in response to movement of the specimen stage; employing the sample generator to generate a plume of specimen material; employing the sample capture cell to capture a sample of the specimen material in the plume; and transporting the sample of the specimen material to an analysis system that is external to the specimen chamber.

In some alternative, additional, or cumulative embodiments, the sample capture cell is moved by a cell-positioning system located inside the specimen chamber.

In some alternative, additional, or cumulative embodiments, the specimen stage is responsive to stage commands from a stage controller, and the cell-positioning system in response to information from the stage controller provides motion to the sample capture cell that is opposite to motion provided by the specimen stage.

In some alternative, additional, or cumulative embodiments, the specimen stage is responsive to stage commands from a stage controller, and the cell-positioning system provides motion to the sample capture cell in response to information associated with a reference signal from an external alignment system that is independent from the stage controller.

In some alternative, additional, or cumulative embodiments, the information associated with the reference signal is conducted into the specimen chamber through an air-sealed conduit.

In some alternative, additional, or cumulative embodiments, the information associated with the reference signal is conducted into the specimen chamber through a wireless connection.

In some alternative, additional, or cumulative embodiments, the specimen chamber has a frame, and the sample of the specimen material is transported through a transport conduit that extends through the frame of the specimen chamber and minimizes drag on the specimen stage.

In some alternative, additional, or cumulative embodiments, the transport conduit employs a sealed piston that extends through the frame of the specimen chamber.

In some alternative, additional, or cumulative embodiments, the information from the stage controller is conducted into the specimen chamber through an air-sealed conduit.

In some alternative, additional, or cumulative embodiments, the information from the stage controller is conducted into the specimen chamber through a wireless connection.

In some alternative, additional, or cumulative embodiments, the cell-positioning system receives commands from a tracking controller located within the specimen chamber.

In some alternative, additional, or cumulative embodiments, the cell-positioning system receives commands from a tracking controller located externally to the specimen chamber.

In some alternative, additional, or cumulative embodiments, the cell-positioning system commands received from the tracking controller are conducted into the specimen chamber through an air-sealed conduit.

In some alternative, additional, or cumulative embodiments, the cell-positioning system commands received from the tracking controller are conducted into the specimen chamber through a wireless connection.

In some alternative, additional, or cumulative embodiments, the cell-positioning system includes at least one of a mechanical actuator, an electro-mechanical actuator, a hydraulic actuator, a pneumatic actuator, a piezoelectric actuator, a magnetic actuator, a linear actuator, a rotary actuator, a ball-screw gear, and a rack and pinion gear.

In some alternative, additional, or cumulative embodiments, the cell-positioning system employs a first cell-positioning subsystem that conveys motion along a first cell-translation axis to the sample capture cell, the cell-positioning system employs a second cell-positioning subsystem that conveys motion along a second cell-translation axis to the sample capture cell, and the first and second cell-translation axes are transverse.

In some alternative, additional, or cumulative embodiments, the specimen stage is a first specimen stage of a specimen-positioning system, the first specimen stage conveys motion along a first stage-translation axis to the specimen chamber, the specimen-positioning system employs a second specimen stage that conveys motion along a second stage-translation axis to the specimen chamber, and the first and second specimen-translation axes are transverse.

In some alternative, additional, or cumulative embodiments, the first cell-translation axis is parallel to the first specimen-translation axis.

In some alternative, additional, or cumulative embodiments, the second cell-translation axis is parallel to the second specimen-translation axis.

In some alternative, additional, or cumulative embodiments, the optical path addresses a first position on the specimen prior to the step of moving the specimen stage, the optical path addresses a second position on the specimen after the step of moving the specimen stage, and the first position and the second position are different.

In some alternative, additional, or cumulative embodiments, the step of moving the specimen stage and the step of moving the sample capture cell are performed simultaneously.

In some alternative, additional, or cumulative embodiments, an imager located externally to the specimen chamber has a field of view over at least a portion of the specimen, and the movement of the specimen stage causes movement of the specimen relative to central axis of the field of view of the imager, and the method further comprises: moving the sample capture cell away from the central axis of the field of view of the imager and away from the capture position relative to the optical path of the sample generator; imaging the specimen along the central axis of the field of view; and moving the sample capture cell to the capture position relative to the optical path of the sample generator.

In some alternative, additional, or cumulative embodiments, the specimen stage, the sample capture cell, the laser ablation site, the cell-positioning system, and the actuator are situated within a specimen chamber that is sealed against ambient atmosphere.

In some alternative, additional, or cumulative embodiments, one or more of a first screw gear coupled to the specimen stage, a carriage coupled to first screw gear and the sample capture cell, and a first motor coupled to the first screw gear are situated within a specimen chamber that is sealed against ambient atmosphere.

In some alternative, additional, or cumulative embodiments, the specimen chamber leaks less than $2.1 \times 10^3$ Pa (0.3 psi) over two minutes after the specimen chamber is pressurized to $4.2 \times 10^3$ Pa (0.6 psi) and sealed.

Additional aspects and advantages will be apparent from the following detailed description of exemplary embodiments, which proceeds with reference to the accompanying drawings.

DETAILED DESCRIPTION OF EXEMPLARY EMBODIMENTS

Figure 1:
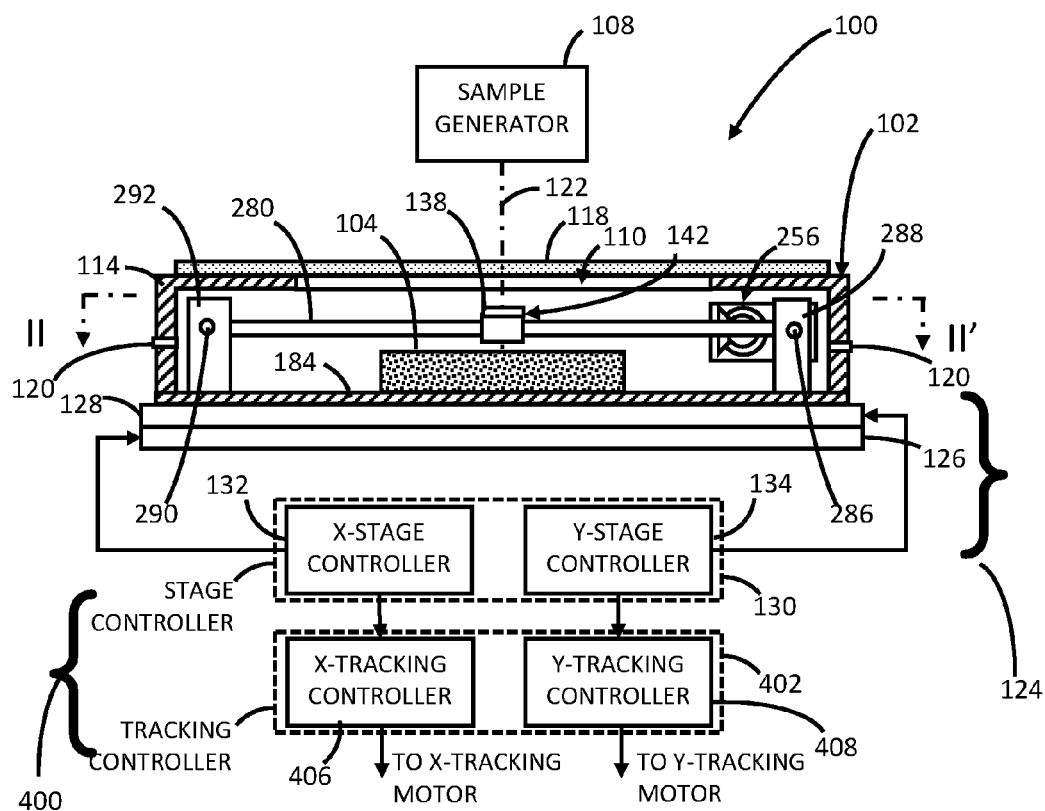
FIG. 1 is a cross-sectional view, taken along line I-I' shown in FIG. 2, schematically illustrating one embodiment of a sampling apparatus, including a specimen chamber and a sample capture cell for handling specimen material ejected from or otherwise generated from the specimen.

Example embodiments are described below with reference to the accompanying drawings. Many different forms and embodiments are possible without deviating from the spirit and teachings of this disclosure and so this disclosure should not be construed as limited to the example embodiments set forth herein. Rather, these example embodiments are provided so that this disclosure will be thorough and complete, and will convey the scope of the disclosure to those skilled in the art. In the drawings, the sizes and relative sizes of components may be may be disproportionate and/or exaggerated for clarity. The terminology used herein is for the purpose of describing particular example embodiments only and is not intended to be limiting. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Unless otherwise specified, a range of values, when recited, includes both the upper and lower limits of the range, as well as any sub-ranges therebetween.

Figure 2:
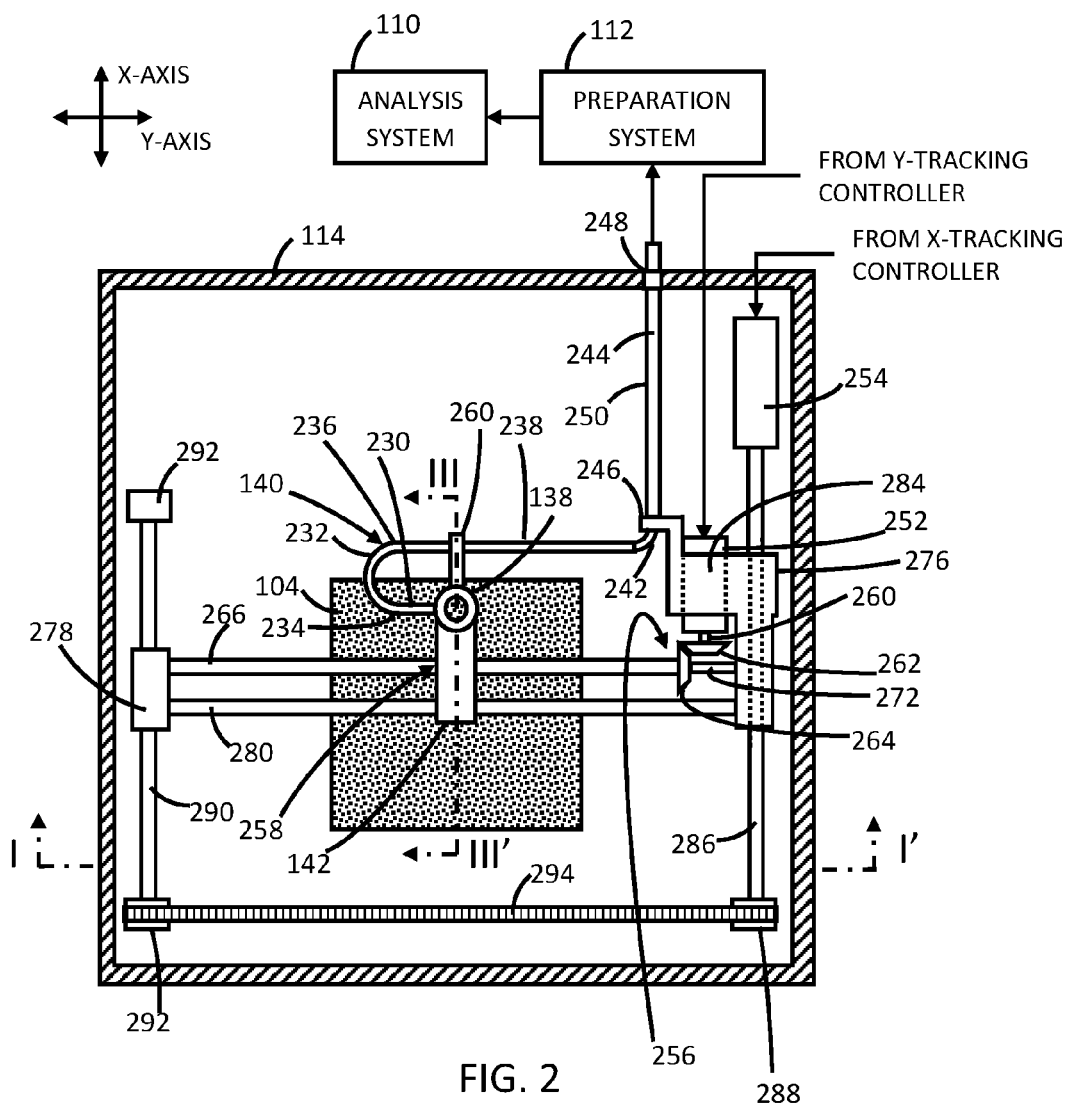
FIG. 2 is a plan view schematically illustrating the sampling apparatus when viewed in the direction indicated along line II-II' in FIG. 1.
Figure 2A:
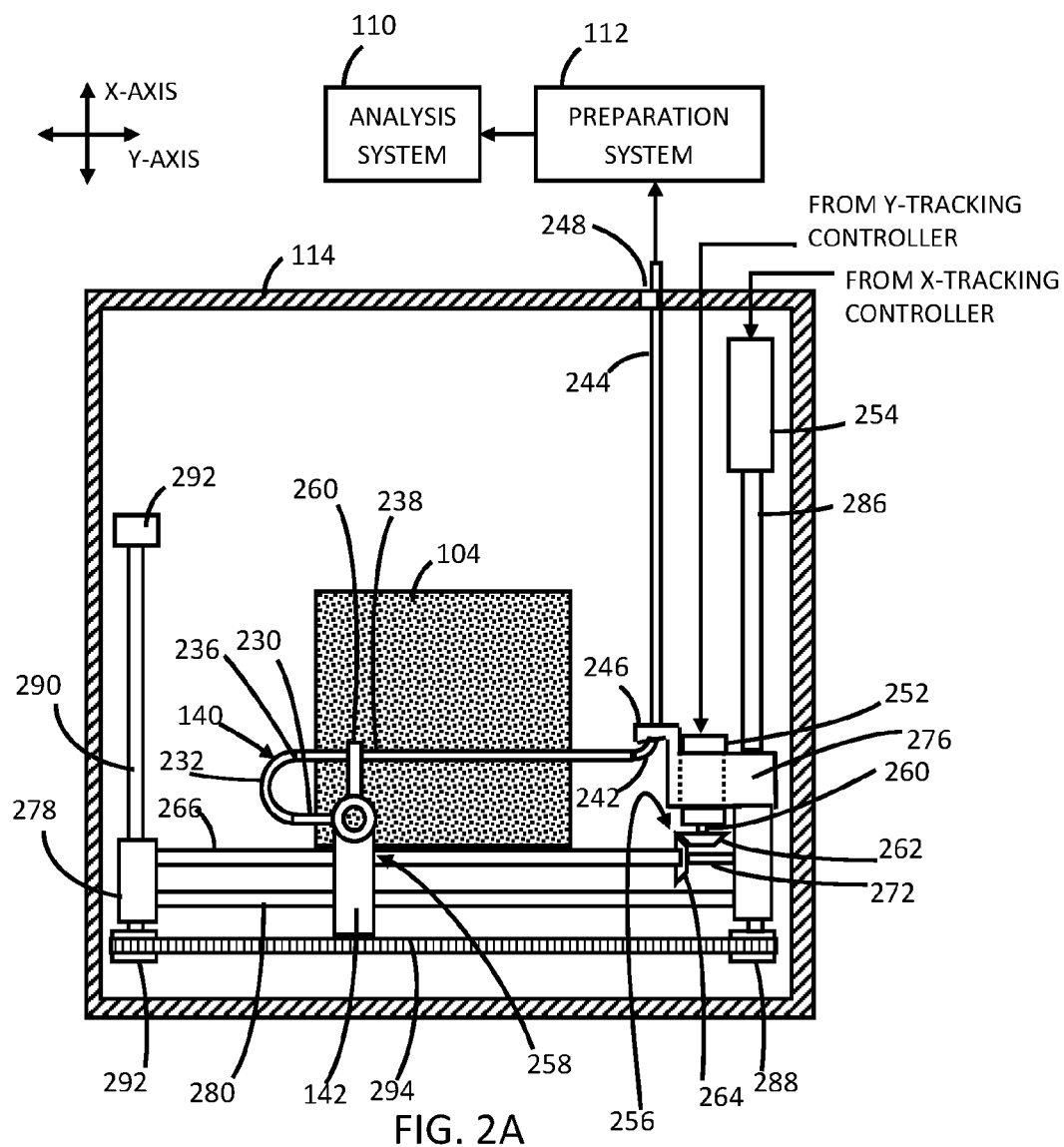
FIG. 2A is a plan view schematically illustrating the sampling apparatus of FIG. 2 with the sample capture cell positioned at a different location with respect to the specimen.

FIG. 1 is a cross-sectional view, taken along line I-I' shown in FIG. 2, schematically illustrating one embodiment of a sampling apparatus 100, including specimen chamber 102 and a sample capture cell 138 for handling specimen material ejected from or otherwise generated from a specimen 104. FIG. 2 is a plan view schematically illustrating the sampling apparatus 100 when viewed in the direction indicated along line II-II' in FIG. 1, and FIG. 2A is a plan view schematically illustrating the sampling apparatus 100 of FIG. 2 with the sample capture cell 138 positioned at a different location with respect to the specimen 104.

With reference to FIG. 1, the sampling apparatus 100, such as for providing samples for LA-ICP-MS or LA-ICP-OES techniques used to analyze the composition of a specimen 104 (e.g., a solid or liquid specimen material). The sampling apparatus 100 may include a specimen chamber 102 configured to accommodate the specimen 104 within an interior 106 of the specimen chamber 102. The sampling apparatus 100 may also include a sample generator 108 configured to dislodge a portion of the specimen 104 (which may be subsequently captured as a sample) and an analysis system 110 configured to analyze a composition of the sample.

Examples of materials that can be provided as the specimen 104 include, for example, archaeological materials, biological assay substrates and other biological materials, ceramics, geological materials, pharmaceutical agents (e.g., pills), metals, polymers, petrochemical materials, liquids, semiconductors, wafers, circuit elements, etc. With reference to FIG. 2, the sampling apparatus 100 may optionally include a sample preparation system 112 configured to excite (e.g., ionize, atomize, illuminate, heat, or the like or a combination thereof) one or more components of the sample before the sample is analyzed by the analysis system 110. The sample preparation system 112 may include a plasma torch (e.g., an ICP torch), or the like. Further, the analysis system 110 may be provided as an MS system, an OES system, or the like, or a combination thereof.

The specimen chamber 102 may include a frame 114 having an optical port 116 extending therethrough to permit optical communication between the sample generator 108 and the interior 106 of the specimen chamber 102. Optionally, a transmission window 118 may be coupled to or supported by the frame 114 to span the optical port 116. The transmission window 118 is typically formed of a material (e.g., quartz) that is at least substantially transparent to laser light generated by the sample generator 108. The transmission window 118 may also be sealed to the frame 114 to prevent dust, debris, or other unwanted gases or other sources of contamination from entering into the interior 106 through the optical port 116. In one embodiment, the transmission window 118 is sealed to the frame 114 also to prevent particles ejected from the specimen 104, vapor generated from the specimen 104, etc., (the particles, vapor, etc., being collectively referred to herein as "specimen material," which is dislodged or removed from the specimen 104), carrier gas, or other fluids present within the interior 106 from exiting the specimen chamber 102 through the optical port 116. Although the frame 114 is illustrated as a single, integrally-formed piece, it will be appreciated that the frame 114 may be formed of multiple components that are coupled together.

The specimen chamber 102 may further include one or more engineered flow inlets, such as injection nozzles 120, each configured to introduce, into the interior 106, a fluid such as a carrier gas (e.g., helium, argon, nitrogen, or the like or a combination thereof) at a flow rate in a range from 20 mL/min to 1000 mL/min (e.g., in a range from 100 mL/min to 150 mL/min, or 125 mL/min, or thereabout). For example, each injection nozzle 120 may be inserted through a fluid port in the frame 114 and may include an inlet configured to be fluidly coupled to a fluid source (e.g., a pressurized fluid source) outside the specimen chamber 102 and an outlet exposed within the interior 106 the specimen chamber 102. Seals (not shown) may be provided between frame and the injection nozzles 120 to fluidly isolate the interior 106 of the specimen chamber 102 from the environment outside the specimen chamber 102. Upon introducing a carrier gas into the interior 106, a flow of the carrier gas (also referred to herein as a "carrier gas flow") is generated within the interior 106. It will be appreciated that the velocity and direction of the carrier gas flow at different locations within the interior 106 can vary depending upon: the shape and size of the interior 106 of the specimen chamber 102, the configuration of the one or more injection nozzles 120, the flow rate with which carrier gas is introduced into the interior 106 by any particular injection nozzle 120, or the like or a combination thereof. In some embodiments, the pressure within the interior 106 can be maintained (e.g., to a pressure less than or equal to $3.5 \times 10^4$ Pa (5 psi)) by controlling the flow rate with which carrier gas is introduced into the interior 106. Moreover, in some embodiments, the pressure within the interior 106 can be maintained to a pressure less than or equal to $2.1 \times 10^4$ Pa (3 psi)) to ease requirements for attaching the transmission window 118, and wherein the pressure approaches the maximum pressure only during a purge cycle. Details regarding exemplary nozzles 120 are disclosed in U.S. Pat. Pub. No. 2014-0223991, which is incorporated herein by reference and which assigned to the assignee of this application. Such nozzles 120 may be available in sampling systems sold by Electro Scientific Industries, Inc. of Portland, Oreg.

In some embodiments, the engineered flow inlets are formed as large slits that disperse the flow through an external baffle system (not shown) to even out the flow across the entire left and right side of the specimen chamber 102. The large slits can be positioned to create even laminar flow for good purge evacuation. Moreover, the large slits can be positioned to create even flow speeds that reach the sample capture cell 138 regardless of where it is in the specimen chamber 102, i.e., the engineered flow inlets provide no dead zones.

The sampling apparatus 100 may further include a specimen positioning system 124 configured to adjust the position of the specimen chamber 102 (and specimen 104) relative to the optical path 122. The specimen positioning system 124 may include one or more specimen positioning stages, such as an X-stage 126 and a Y-stage 128, that may be configured to linearly translate the specimen 104 along at least one direction (e.g., respectively, an X-direction, a Y-direction orthogonal to the X-direction, or the like or a combination thereof) relative to the optical path 122, or may be configured to rotate the specimen 104 relative to the optical path 122, or the like or a combination thereof. The specimen positioning stage or stages 126 and 128 may be responsive to one or more stage controllers 130, such as respective X-stage controller 132 and Y-stage controller 134.

Suitable specimen positioning systems 124 and stage controllers 130 are commercially available individually or together. Exemplary specimen positioning systems include, but are not limited to, members of the MX80L™ miniature stage series sold by the Parker Hannifin Corp. of Cleveland, Ohio; members of the METROSTAGE™ series sold by Nutec Components, Inc. of Deer Park, N.Y.; members of the XY-6060™ series sold by Dover Motion of Boxborough, Mass.; and X-Y stages sold by HiWIN Corporation of Elgin, Ill.

Although the sampling apparatus 100 is illustrated as including the specimen positioning system 124, it will be appreciated that the specimen positioning system 124 may be omitted, modified, or substituted for any other suitable or beneficial mechanism for adjusting the position of the specimen 104 relative to the optical path 122.

In some embodiments, the specimen positioning system 124 may also optionally include a specimen holder configured to support the specimen 104 within the specimen chamber 102, a carriage configured carry the specimen holder, a base configured to support the carriage within the interior 106 and a positioning stage configured to move the carriage. Details regarding such carriage systems are disclosed in U.S. Pat. Pub. No. 2014-0227776, which is incorporated herein by reference and which assigned to the assignee of this application. Such carriages may be available in sampling systems sold by Electro Scientific Industries, Inc. of Portland, Oreg.

Optionally, a height-adjustment mechanism (not shown), such as a micrometer, can be coupled to the specimen positioning system 124 to adjust a position of the specimen 104 along a vertical direction (e.g., along the optical path 122) to ensure that the specimen 104 is arranged at a suitable or beneficial height location within the interior 106.

The specimen positioning system 124 ensures repeatable lateral and/or angular movement and positioning of the specimen 104 within the interior 106, with low movement lag and motion hysteresis.

The sample generator 108 is configured to direct laser light along the optical path 122, through the optical port 116 and into the interior 106 of the specimen chamber 102 to impinge upon the specimen 104. The laser light may be directed along the optical path 122 as one or more laser pulses generated by one or more lasers. One or more characteristics of the laser pulses may be selected or otherwise controlled to impinge a region of the specimen 104 to ablate a portion of the specimen 104. Characteristics that may be selected or otherwise controlled may, for example, include wavelength (e.g., in a range from about 157 nm to about 11 μm, such as 193 nm, 213 nm, 266 nm, or the like), pulse duration (e.g., in a range from about 100 femtoseconds to about 25 nanoseconds), spot size (e.g., in a range from about 1 μm to about 9 mm, or the like), pulse energy, average power, peak power, temporal profile, etc. The sample generator 108 may also include laser optics (e.g., one or more lenses, beam expanders, collimators, apertures, mirrors, etc.) configured to modify laser light generated by one or more of the lasers. As used herein, a region of the specimen 104 that is impinged by a laser pulse may be referred to as a "laser ablation site." Upon being ablated, specimen material is removed from a region of the specimen 104 located within or adjacent to the laser ablation site to form a plume containing the specimen material.

With reference to FIG. 2, to facilitate handling of the specimen material (e.g., so that the composition of the specimen material can be analyzed at the analysis system 110), the sampling apparatus 100 may include a sample capture cell 138 configured to capture the specimen material when it is arranged operably proximate to the specimen 104. Specimen material captured by the sample capture cell 138 is also herein referred to as a "sample" or a "specimen sample." The sampling apparatus 100 may further include a transport conduit 140 (also referred to as an "extraction tube") configured to transport the sample to the sample preparation system 112. In some embodiments, the sampling apparatus 100 may include a cell support 142 to support the sample capture cell 138 within the interior 106 of the specimen chamber 102 at a desired location and height above the specimen 104.

In one embodiment, the optional height-adjustment mechanism may be used to adjust the height of one or more of the stages 126 and 128 (and, thus, the specimen 104) relative to the cell support 142 (and thus the sample capture cell 138) to ensure that the sample capture cell 138 is operably proximate to the specimen 104. In another embodiment, a height adjustment mechanism such as a micrometer, may be optionally provided to adjust a position of the sample capture cell 138 relative to the specimen 104 (e.g., along the optical path 122) to ensure that the the cell support 142 (and thus the sample capture cell 138) is arranged at a suitable or beneficial position within the interior 106. Thus, in addition to (or instead of) adjusting a position of the specimen 104 relative to the sample capture cell 138, the position of the sample capture cell 138 relative to the specimen 104 may be adjusted to ensure that the sample capture cell 138 is operably proximate to the specimen 104.

In one embodiment the sample capture cell 138 is operably proximate to the specimen 104 when the sample capture cell 138 is spaced apart from the specimen 104 by a gap distance in a range from 0.01 mm to 1 mm (e.g., in a range from 0.05 mm to 0.2 mm, or in a range from 0.1 mm to 0.2 mm). It will be appreciated, however, that depending on factors such as the carrier gas flow velocity within a region of the interior 106 between the sample capture cell 138 and the specimen 104, the gap distance can be less than 0.01 mm or greater than 1 mm. In some embodiments, the sample capture cell 138 may even contact the specimen 104.

Figure 3:
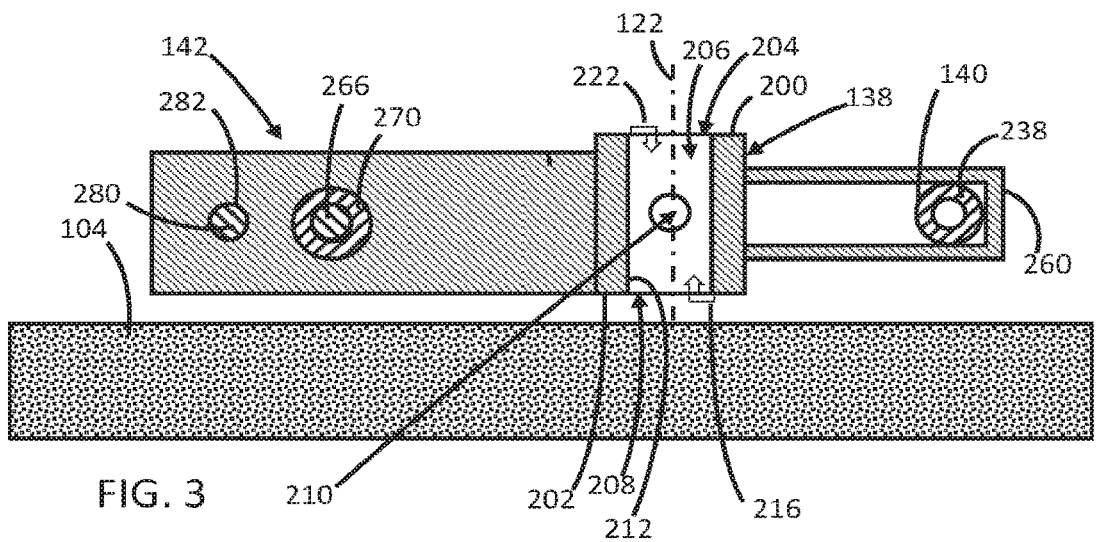
FIG. 3 is a cross-sectional view, taken along line III-III' shown in FIG. 1, schematically illustrating a portion of the apparatus shown in FIG. 2, including the sample capture cell, positioned above a portion of the specimen.

FIG. 3 is a cross-sectional view, taken along line III-III' shown in FIG. 1, schematically illustrating a portion of the apparatus shown in FIG. 2, including the sample capture cell 138, positioned above a portion of the specimen 104. With reference to FIG. 3, the sample capture cell 138 may generally be characterized as having an upper surface 200 (e.g., configured to generally face toward the sample generator 108) and a lower surface 202 (e.g., configured to generally face toward the specimen 104), a front end region and a back end region opposite the front end region. Generally, the sample capture cell 138 is arranged within the interior 106 such that the front end region is disposed upstream of the back end region, relative to the predominant direction of the carrier gas flow at the location in the interior 106 where the sample capture cell 138 is arranged.

In some embodiments, a surface of the sample capture cell 138 defining the front end region is configured so as to be convexly-curved. For example, the surface of the sample capture cell 138 defining the front end region is circularly curved, centered on an axis of a second inlet 204. In some examples, the curvature may exhibit a radius in a range from about 1.2 mm to about 1.5 mm. It will be appreciated, however, that depending on factors such as the predominant direction of the carrier gas flow at the location in the interior 106 where the sample capture cell 138 is arranged, the location of its capture cavity 206 within the sample capture cell 138, and other dimensions of the sample capture cell 138, the geometric configuration of the surface defining the front end region of the sample capture cell 138 may be varied in any manner that may be suitable or beneficial. Moreover, the geometric configuration the sample capture cell 138 as a whole need not be cylindrical and can be any shape, such as cuboidal, ellipsoidal, or pyramidal, that is suitable for sample capture.

It will also be appreciated that the location of the sample capture cell 138 within the interior 106 can be selected based upon factors such as the geometry of the interior 106 and the number and location of injection nozzles 120 generating the carrier gas flow within the interior 106. For example, if the interior 106 has a cylindrical geometry, and if only one injection nozzle 120 is used to introduce carrier gas into the interior 106 along the diameter of the cylindrical interior 106 at the aforementioned flow rate, then the sample capture cell 138 can be located at or near the center of the interior 106.

According to some embodiments, the sample capture cell 138 may further include a first inlet 208 in fluid communication with the capture cavity 206, an outlet 210 in fluid communication with the capture cavity 206, and a guide wall 212 exposed within the capture cavity 206. In some embodiments, the sample capture cell 138 may further include a second inlet 204 in fluid communication with the capture cavity 206. In some embodiments, the sample capture cell 138 can be provided as a monolithic body formed of any suitable material such as a glass, a ceramic, a polymer, a metal, or the like, or a combination thereof. Moreover, two or more or all of the capture cavity 206, the first inlet 208, the second inlet 204, the outlet 210, and the guide wall 212, may be integrally formed within the body by conventional techniques (e.g., by machining, grinding, cutting, drilling, 3-D printing, etc.). In other embodiments, however, two or more or all of the capture cavity 206, the first inlet 208, the second inlet 204, the outlet 210, and the guide wall 212, may be separately formed from different components, which are subsequently coupled together.

The capture cavity 206 extends from the first inlet 208 formed in the lower surface 202 of the sample capture cell 138 and is configured to receive the plume containing the specimen material ejected or otherwise generated from the laser ablation site on the specimen 104 when the sample capture cell 138 is arranged operably proximate to the specimen 104. In an embodiment in which the sample capture cell 138 is spaced apart from the specimen 104, carrier gas adjacent to the specimen 104 can be also be transmitted into the capture cavity 206 through the first inlet 208. In some embodiments, the guide wall 212 defines the extent (e.g., lateral, vertical, etc.) of the capture cavity 206 within the sample capture cell 138. In some embodiments, the volume of the capture cavity 206 can be in a range from $0.001 \text{ cm}^3$ to $1 \text{ cm}^3$ (e.g., $0.005 \text{ cm}^3$, or thereabout). It will be appreciated, however, that depending on factors such as the carrier gas flow velocity within the region of the interior 106 where the sample capture cell 138 is located, the size of the plume of specimen material, etc., the volume of the capture cavity 206 can be less than $0.001 \text{ cm}^3$ or greater than $1 \text{ cm}^3$.

In some embodiments, the first inlet 208 may be spaced apart or extend from the capture cavity 206 to a surface of the sample capture cell 138 and may be configured to transmit a surface flow 216 of the carrier gas from a first location near the capture cavity 206 of the sample capture cell 138. In some embodiments, the first inlet 208 may extend vertically from the lower surface 202 toward the upper surface 200 to a height, such as about 1 mm, and may extend horizontally between the lower surface 202 and upper surface 200 across a width, such as about 2.2 mm. It will be appreciated, however, that depending on factors such as the carrier gas flow velocity within a region of the interior 106 at the first location, the size and shape of any portion of the first inlet 208 may be modified in any suitable or beneficial manner. In some embodiments, the first inlet 208 may be configured to transmit the surface flow 216 into the capture cavity 206 along a first direction that is generally (or at least substantially) parallel to a surface of the specimen 104. Although the first inlet 208 may be spaced apart from the lower surface 202 toward the upper surface 200, it will be appreciated that, in other embodiments, the first inlet 208 may not be spaced apart from the lower surface 202.

In some embodiments, the second inlet 204 extends from the capture cavity 206 to the upper surface 200 of the sample capture cell 138. Accordingly, the second inlet 204 is configured to transmit a secondary flow 222 of the carrier gas from a second location, near to the upper surface 200 of the sample capture cell 138, into the capture cavity 206. In some embodiments, the second inlet 204 is a configured as a circular tube having a diameter, such as in a range from about 0.5 mm to about 0.85 mm, aligned with and extending along the optical path 122 from the capture cavity 206 to the upper surface 200 to a height, such as about 2 mm. It will be appreciated, however, that depending on factors such as the carrier gas flow velocity within the interior 106 at the second location, the size and shape of any portion of the second inlet may be modified in any suitable or beneficial manner.

In some embodiments, the second inlet 204 is configured to transmit the flow of the carrier gas into the capture cavity 206 along a second direction that is generally (or at least substantially) perpendicular to a surface of the specimen 104. In other embodiments, however, the second inlet 204 may be configured to transmit the flow of the carrier gas into the second region 224 of the capture cavity 206 along a second direction that is substantially oblique to a surface of the specimen 104. Further, the second inlet 204 may be configured such that the sample generator 108 is in optical communication with a region of the specimen 104 (e.g., along the optical path 122) through the second inlet 204 and the capture cavity 206. Accordingly, laser light may be directed from the sample generator 108 along the optical path 122, through the second inlet 204 and the capture cavity 206 to impinge upon the specimen 104 at a laser ablation site. When the directed laser light impinges the specimen 104 at the laser ablation site, a plume containing the specimen material ejected or otherwise generated from the specimen 104 emanates from the surface of the specimen 104.

Depending on factors such as the material of the specimen 104, characteristics of the directed laser light 300, the velocity of the carrier gas flow, etc., vertical expansion of the plume may occur very rapidly. For example, the plume may extend to a height above the specimen 104, such as about 2 mm, within less than 2 ms (e.g., about 0.5 ms) after the directed laser light impinges the specimen 104 at the laser ablation site. By transmitting a flow of the carrier gas through the second inlet 204 into the capture cavity 206, the vertical expansion of the plume may be prevented or otherwise minimally re-entrained, thereby reducing or minimizing the volume that the plume of specimen material would otherwise occupy within the capture cavity 206. By reducing or minimizing the volume that the plume of specimen material occupies within the capture cavity 206, the specimen material within the plume can be efficiently captured and transferred into the outlet 210.

The outlet 210 extends from a surface of the sample capture cell 138 to a back end region of the guide wall 212 exposed within the capture cavity 206. Accordingly, the outlet 210 is configured to receive carrier gas from the capture cavity 206 so that the received carrier gas can be transmitted to a location outside the sample capture cell 138 (e.g., via the transport conduit 140). In some embodiments, the outlet 210 may be configured to accommodate a portion of the transport conduit 140. In some embodiments, the outlet 210 and the transport conduit 140 are adapted to accommodate an outlet conduit seal (not shown).

The guide wall 212 is configured to deflect, vector, or otherwise direct one or more flows of the carrier gas introduced into the capture cavity 206 (e.g., via one or more of the first inlet 208 and the second inlet 204) such that at least a portion of the plume of specimen material received within the capture cavity 206 is entrained by the directed flow of carrier gas, thereby so as to be transferrable into the outlet 210. For purposes of discussion herein, specimen material transferred into the outlet 210 is "captured" by the sample capture cell 138 and, therefore, may also be referred to as a "sample" of the specimen 104 or as a "specimen sample." In some embodiments, the guide wall 212 is configured to direct the one or more flows of the carrier gas such that the flow of carrier gas into the plume or into the outlet 210 is laminar or quasi-laminar. In other embodiments, however, the guide wall 212 is configured to direct the one or more flows of the carrier gas such that the flow of carrier gas into the plume or into the outlet 210 is turbulent. Similarly, one or more of the aforementioned features of the sample capture cell 138 (e.g., the lower surface 202, the guide wall 212, the first inlet 208, the second inlet 204, or the like) may be configured such that the flow of carrier gas over the surface of the specimen 104 and outside the capture cavity 206 is laminar, quasi-laminar, turbulent, or a combination thereof. Additional details concerning sample capture cells 138 are disclosed in U.S. Pat. Pub. No. 2014-0227776, which is incorporated herein by reference and which assigned to the assignee of this application. Such capture cells 138 may be available in sampling systems sold by Electro Scientific Industries, Inc. of Portland, Oreg.

In some embodiments, the sample capture cell 138 is coupled to the transport conduit 140 so that the sample transferred into the outlet 210 can be transported to a location outside the sample capture cell 138 (e.g., via the transport conduit 140 to the sample preparation system 112). To couple the transport conduit 140 to the sample capture cell 138, an end of the transport conduit 140 (also referred to as a "first end" or a "sample receiving end") can be inserted through an outlet conduit seal (not shown). Upon coupling the transport conduit 140 to the sample capture cell 138 in the manner described above, the carrier gas received at the outlet 210 can also be received within the transport conduit 140 and transported to a location outside the specimen chamber 102 (e.g., to the sample preparation system 112). In addition to the sample receiving end, the transport conduit 140 may further include a second end (also referred to herein as a sample injection end) that is down stream of the sample receiving end.

In some embodiments, the transport conduit 140 has an inner diameter in a range from 50 μm to 1 mm (e.g., in a range from 50 μm to 500 μm, or 250 μm, or thereabout). However, depending on factors such as the pressure within the interior 106 and the length of the transport conduit 140, the inner diameter of the transport conduit 140 may be less than 50 μm or greater than 1 mm. The inner diameter of the transport conduit 140 at the sample receiving end may be same or different (i.e., larger or smaller) than the inner diameter of the transport conduit 140 at the sample injection end. Further, the inner diameter of the transport conduit 140 may be at least substantially constant along the length thereof, or may vary.

In some embodiments, the transport conduit 140 may be provided as a single flexible tube having no valves between the sample receiving end and sample injection end. Exemplary tubing that can be used for the transport conduit 140 includes, but is not limited to, Tygon® B-44-3 tubing 1/16"×1/8," fused silica capillary tubing 250 μm (inner diameter), or BT250370™ made by Biotaq of Gaithersburg, Md.

In some embodiments, the transport conduit 140 may be provided as a mix of flexible and rigid tubular segments (having no valves or a limited number of valves between the sample receiving end and sample injection end). Additional exemplary materials from which some segments of the transport conduit 140 can be formed include one or more materials selected from the group consisting of a glass, a polymer, a ceramic and a metal. In some embodiments, however, some segments of the transport conduit 140 are formed of fused glass. In another embodiment, some segments of the transport conduit 140 are formed of a polymer material such as a fluoropolymer (e.g., perfluoroalkoxy, polytetrafluoroethylene, or the like or a combination thereof), polyethylene terephthalate, or the like, or a combination thereof. In yet another embodiment, some segments of the transport conduit 140 are formed of a ceramic material such as alumina, sapphire, or the like, or a combination thereof. In some embodiments, some segments of the transport conduit 140 are formed of a metal material such as stainless steel, copper, platinum, or the like, or a combination thereof.

In some embodiments, the transport conduit 140 may have an initial segment 230 that is substantially straight (i.e., an axis of an initial segment 230 of the transport conduit 140 is substantially collinear with an axis through a center of the outlet 210) from the sample receiving end for a length (defined from the sample receiving end). In some embodiments, the length of the initial segment 230 is at least in a range from 2 mm to 200 mm (e.g., in a range from 5 mm to 100 mm, or in a range from 5 mm to 60 mm, or in a range from 2 mm to 50 mm, or in a range from 2 mm to 45 mm, or thereabout). It will be appreciated, however, that depending on factors such as the pressure within the interior 106, the inner diameter of the transport conduit 140, the configuration of the specimen chamber 102 and the sample preparation system 112, the length of the initial segment 230 of the transport conduit 140 may be less than 2 mm or greater than 200 mm. The initial segment 230 may have an inner diameter that is the same range as that of the transport conduit 140 as a whole. Moreover, the initial segment 230 may have an inner diameter that is the same as that of the transport conduit 140 as a whole or may have an inner diameter that is different from that of other segments of the transport conduit 140. The initial segment 230 can be rigid or flexible.

In some embodiments, the initial segment 230 may be integrated with or coupled to a constant curvature segment 232 of the transport conduit 140. The constant curvature segment 232 may have a radius of curvature between proximal and distal curvature endpoints 234 and 236 in a range from about 15 mm to about 25 mm, and more particularly in a range from about 17 mm to about 23 mm. The constant curvature segment 232 may have an inner diameter that is the same as or is different from that of the initial segment 230. In some embodiments, the constant curvature segment 232 has a semicircular profile; however, the profile can alternatively form an arc of less than 180 degrees or more than 180 degrees or have any suitable shape. The constant curvature segment 232 may have an inner diameter that is in the same range as that of the transport conduit 140 as a whole. Moreover, the constant curvature segment 232 may have an inner diameter that is the same as that of the transport conduit 140 as a whole or may have an inner diameter that is different from that of other segments, such as the initial segment 230, of the transport conduit 140. The constant curvature segment 232 may be provided as a rigid or flexible material. However, if a flexible material is employed for the constant curvature segment 232, then the constant curvature segment 232 may be supported by a rigid sleeve (not shown) to maintain the constant curvature.

In some embodiments, the constant curvature segment 232 may be integrated with or coupled to a post-curve segment 238 of the transport conduit 140. The post-curve segment 238 may be substantially straight (i.e., an axis of post-curve segment 238 of the transport conduit 140 is substantially collinear with an axis through a center of the distal endpoint 236 of the constant curvature segment 232) from the distal endpoint 236 for a length (defined from the sample receiving end). In some embodiments, the length of post-curve segment 238 is at least in a range from 2 mm to 200 mm (e.g., in a range from 5 mm to 100 mm, or in a range from 5 mm to 60 mm, or in a range from 2 mm to 50 mm, or in a range from 2 mm to 45 mm, or thereabout). It will be appreciated, however, that depending on factors such as the pressure within the interior 106, the inner diameter of the transport conduit 140, the configuration of the specimen chamber 102 and the sample preparation system 112, the length of the post-curve segment 238 of the transport conduit 140 may be less than 2 mm or greater than 200 mm. In some embodiments, the length of the post-curve segment 238 is longer than the length of the initial segment 230. In some embodiments, the initial segment 230, the constant curvature segment 232, and the post-curve segment 238 may lie in the same plane; however, in some embodiments, one or more of the initial segment 230, the constant curvature segment 232, and the post-curve segment 238 may lie in different planes.

The post-curve segment 238 may have an inner diameter that is in the same range as that of the transport conduit 140 as a whole. Moreover, the post-curve segment 238 may have an inner diameter that is the same as that of the transport conduit 140 as a whole or may have an inner diameter that is different from that of other segments, such as the initial segment 230 or the constant curvature segment 232, of the transport conduit 140.

With reference to FIG. 2A, in some embodiments, the post-curve segment 238 is made of a material of sufficient flexibility to extend to a length that is greater than or equal to at least 90% of a length of a side of the specimen chamber 102. In some embodiments, the post-curve segment 238 is made of a material of sufficient flexibility to extend to a length that is greater than or equal to at least 90% a length of a side of the specimen 104. In some embodiments, the properties of the material permit the length of the post-curve segment 238 to be lengthened without substantially decreasing the inner diameter of the post-curve segment 238.

The flexibility of the post-curve segment 238 permits the sample capture cell 138 to be movable along a first axis over the specimen 104, as later discussed in greater detail. For convenience, X- and Y-axes of the exemplary sampling apparatus 100 have been labeled in FIGS. 2 and 2A. In the illustrated example, the first axis is arbitrarily selected to be the Y-axis. Skilled practitioners will appreciate that the labeled axes are arbitrary and can be exchanged or even rotated.

With reference again to FIGS. 2, 2A, and 3, the cell support 142 may be provided with a segment bracket 260 for supporting the post-curve segment 238 of the transport conduit 140. The segment bracket 260 may help maintain alignment of the post-curve segment 238 with the constant curvature segment 232 and a downstream turn segment 242.

The segment bracket 260 may also help ameliorate any sag that may be exhibited by the flexible material of the post-curve segment 238.

In some embodiments, the turn segment 242 may be integrated with or coupled to the post-curve segment 238 of the transport conduit 140. The turn segment 242 may have constant curvature, which in some embodiments results in a 90-degree turn of the transport conduit 140.

The turn segment 242 may be supported by a turn bracket 246 that may help maintain alignment of the turn segment 242 with the post-curve segment 238 and a downstream outflow segment 244. The turn segment 242 may also be integrated with or coupled to the outflow segment 244 that is arranged between the turn segment 242 of the transport conduit 140 and the preparation system 112. Moreover, the outflow segment 244 may be transverse or perpendicular to the post-curve segment 238.

Some or all of the post-curve segment 238, the turn segment 242, and the outflow segment 244 may be positioned in the same plane. Some or all of the post-curve segment 238, the turn segment 242, and the outflow segment 244 may have the same inner diameter.

In some embodiments, the outflow segment 244 is made of a material of sufficient flexibility to extend to a length that is greater than or equal to at least 90% of a length of a side of the specimen chamber 102. In some embodiments, the outflow segment 244 is made of a material of sufficient flexibility to extend to a length that is greater than or equal to at least 90% a length of a side of the specimen 104. In some embodiments, the properties of the material permit the length of the outflow segment 244 to be lengthened without substantially decreasing the inner diameter of the outflow segment 244. In some embodiments, the turn bracket 246 may be employed to support the outflow segment 244 instead of or in addition to the turn segment 242. A portal 248 in the frame 114 may support the outflow segment 244 toward its outflow end and provide passage of the outflow segment 244 through the frame 114 to the preparation system 112.

The flexibility of the outflow segment 244 permits the sample capture cell 138 to be movable along a second axis over the specimen 104, as later discussed in greater detail. In the illustrated example, the second axis is arbitrarily selected to be the X-axis.

In some embodiments, one or more of the post-curve segment 234 and the outflow segment 244 may be supported by respective rigid sleeves that may cover a portion (or the entirety) of the respective lengths of the post-curve segment 234 and the outflow segment 244 when the flexible material of the respective post-curve segment 234 and the outflow segment 244 is relaxed.

In some embodiments, either or both of the post-curve segment 234 and the outflow segment 244 of transport conduit 140 comprise rigid material that cooperate with rigid inner or outer extension sleeves that permit elongation of the transport conduit 140 along the first and second axes. In some embodiments, the transport conduit 140 is routed through a constant curvature constraint holder and connects to a sliding seal piston 250 that is pushed and pulled through the frame 114 by a cup drive motor 252.

Constructed as exemplarily described above, the transport conduit 140 can efficiently transport a sample from the sample capture cell 138 to the sample preparation system 112. Efficient capture and transfer of a sample from a laser ablation site to the transport conduit 140, coupled with efficient transport of the sample from the sample capture cell 138 to the sample preparation system 112, can enable the analysis system 110 to generate signals (e.g., corresponding to the composition of specimen sample) that have relatively short peak widths (e.g., in a range from about 10 ms to about 20 ms (e.g., 12 ms, or thereabout), measured relative to a baseline where 98% of the total signal is observed within 10 ms) and correspondingly fast wash-out times. Generating signals having such relatively short peak widths and fast wash-out times, can help to facilitate high-speed and high sensitivity compositional analysis of the specimen 104. Similarly, depending on factors such as the pressure within the interior 106 and the length of the transport conduit 140, the inner diameter of the transport conduit 140, the peak width may be beneficially increased to 1 s or thereabout.

As previously described, the specimen 104 and its surrounding specimen chamber 102 may be positioned relative to the optical path 122 of the ablating laser by one or more of the X-stage 126 and the Y-stage 128. With reference again to FIGS. 1, 2, 2A, and 3, the cell support 142 (and the sample capture cell 138 it supports) can be moved to offset movement of the frame 114 by one or both of the specimen positioning stages 126 and 128 to maintain alignment of the sample capture cell 138 at a fixed location with respect to the optical path 112. However, the cell support 142 (and the sample capture cell 138) can also be controlled to move independently from the movement of the specimen positioning stages 126 and 128.

In some embodiments, the cell support 142 can be moved by a cell-positioning system that may include one or more cell-positioning subsystems, such as a motion-translation system 256, e.g. an actuator such as a device or an assembly of devices that convert motion into linear motion to execute movement. Exemplary motion-translation systems 256 include one or more electro-mechanical actuators, such as a rack and pinion system, a screw and traveling nut system, or a ball-screw drive system, etc. In some embodiments, the motion-translation system 256 may alternatively or additionally include one or more of a hydraulic actuator, a pneumatic actuator, a piezoelectric actuator, or a magnetic actuator. Moreover, these actuators may be linear actuators or rotary actuators. These systems and/or their components may be commercially available.

In some embodiments, the motion-translation system 256 exhibits very high positional repeatability. In some embodiments of an open loop configuration, the motion-translation system 256 can be accurate to about 200 μm or smaller. In some embodiments of an open loop configuration, the motion-translation system 256 can be accurate to about 100 μm or smaller. In some embodiments of an open loop configuration, the motion-translation system 256 can be accurate to about 50 μm or smaller. In some embodiments of an open loop configuration, the motion-translation system 256 can be accurate to about 20 μm or smaller. In some embodiments of an open loop configuration, the motion-translation system 256 can be accurate to about 10 μm or smaller. It will be appreciated that closed-loop configurations can provide much greater accuracy; however, closed-loop systems typically entail much greater costs.

In some embodiments, the cell-positioning system may employ one or more motors positioned within the specimen chamber 102, such as cup drive motors 252 and 254, to move the sample capture cell 138. In some embodiments, one or both of the cup drive motors 252 and 254 may be stepper motors, direct current motors with an encoder, or the like, or any combination thereof. In some embodiments, the accuracy of the cup drive motors 252 and 254 may be repeatable to 6 μm or better. However, the cup drive motors 252 and 254 may have better or worse repeatability. In some embodiments, the position of the sample capture cell 138 may be relatively insensitive to signal data quality. For example, in some embodiments, an ICPMS signal does not vary over 3 mm of variation in the position of the sample capture cell 138. An exemplary cup drive motor 252 or 254 includes, but is not limited to, an AM1020-V-12-250-08™ with a 64:1 gear head sold by MicroMo of Clearwater, Fla. However, other brands or types of motors could be employed.

For convenience of description, the cup drive motor 252 may be referred to as a Y-axis motor 252, and the cup drive motor 254 may be referred to as an X-axis motor 254. In some embodiments, the Y-axis motor 252 and the X-axis motor 254 employ identical motors. In some embodiments, the Y-axis motor 252 and the X-axis motor 254 employ the same type of motor, but the motors have different specifications. In some embodiments, the Y-axis motor 252 and the X-axis motor 254 employ different types of motors.

In some embodiments, a first cell-positioning subsystem includes the Y-axis motor 252 that may translate motion from its motor shaft 260 to the cell support 142 through a ball-screw drive system 258, and one or more bevel gears 262 and 264. In the illustrated embodiment, the bevel gear 262 engages the bevel gear 264 and translates motion of the motor shaft 260 to a threaded shaft 266, which may be oriented transversely to the motor shaft 260. In some embodiments, the threaded shaft 266 is perpendicular to the motor shaft 260. In some embodiments, the threaded shaft 266 and the motor shaft 260 lie in the same plane. In some embodiments, the threaded shaft 266 and the motor shaft 260 lie in different planes.

In some embodiments, the cell support 142 may include a ball-bearing assembly 270 that acts as a nut about the threaded shaft 266. Thus, whenever the Y-axis motor 252 turns the bevel gear 262, the bevel gear 264 transfers the motion to the threaded shaft 266 and causes the cell support 142 move along the threads of the threaded shaft 226, causing the sample capture cell 138 to travel along the Y-axis defined by the threaded shaft 266.

In some embodiments, the threaded shaft 266 may be supported, through a shaft extension 272, between a motor support carriage 276 and an auxiliary carriage 278. The motor support carriage 276 and the auxiliary carriage 278 may also support a guide rail 280 between them that passes through an aperture 282 within the cell support 142. The guide rail 280 may have a circular profile but other profiles are possible. The guide rail 280 could be a threaded or non-threaded rod. In some embodiments, the guide rail 280 and the threaded shaft 266 lie in the same plane, which may be generally parallel to the surface of the specimen 104 or a bottom surface 184 of the frame 114. However, the guide rail 280 and the threaded shaft 266 need not lie in the same plane. The rail 280 and the threaded shaft 266 may be located on the same side of the sample capture cell 138, or the sample capture cell 138 may be located between the guide rail 280 and the threaded shaft 266.

In some embodiments, a mechanical link (not shown) couples the guide rail 280 to the motion-translation system 256 such that the Y-axis motor 252 causes rotation of the guide rail 280 as well as rotation of the threaded shaft 266. In some embodiments, the mechanical link couples the guide rail 280 to the threaded shaft 266 such that rotation of the threaded shaft 266 causes a corresponding rotation of the guide rail 280. In some embodiments, the mechanical link is a chain (e.g., a roller chain), track, or other perforated or indented material. In some embodiments, each of the guide rail 280 and the threaded shaft 266 is provided with a sprocket that engages with the mechanical link. In some embodiments, the mechanical link is a cable or belt. In some embodiments, each of the guide rail 280 and the threaded shaft 266 is provided with a pulley that engages with the mechanical link. In some embodiments, the mechanical link is an assembly of gears.

In some embodiments, the rail 280 and the threaded shaft 266 hold the cell support 142 in a manner to provide a fixed elevation and a level orientation for the sample capture cell 138. In other embodiments, the motor support carriage 276 and the auxiliary carriage 278 (and any structures that support them) may be constructed to provide for an elevation-positioning system (not shown) to adjust the elevation of the sample capture cell 138 with respect to the surface of the specimen 104. Such elevational positioning could employ multiple coordinated Z-axis actuators. Such elevation-positioning adjustment may be useful for adjusting to the idiosyncrasies of the particular laser and the plumes it creates, or to adjust for differences in the plumes created from different materials due to different laser-material interactions.

The motor support carriage 276 may be a single unit or a composite of multiple parts. In some embodiments, the motor support carriage 276 includes: a motor housing 284 for housing the cup drive motor 252; the turn bracket 242 that supports the transport conduit 140; sockets to support the rail 280 and the shaft extension 272 of the threaded shaft 266; a socket, screw, or other connector to support the sliding seal piston 250; and an aperture to support a threaded shaft 286. Supports 288 for the threaded shaft 286 and the cup drive motor 254 may be anchored to the bottom surface 184 of the specimen chamber 102 on Z-axis actuators, as previously discussed.

In some embodiments, the cell support 142 (and the sample capture cell 138) can additionally or alternatively be moved along an axis transverse to that utilized by the threaded shaft 266 of a second cell-positioning subsystem. In particular, in some embodiments, the second cell-positioning subsystem employs one or more cup drive motors 254 to adjust the X-axis position of the sample capture cell 138 with respect to the specimen 104. In some embodiments, the aperture of the motor support carriage 276 may house a ball-bearing assembly (not shown) that acts as a nut about the threaded shaft 286. Thus, whenever the X-axis motor 254 turns, it engages the threaded shaft 286 and causes motor support carriage 276 to move along the threads of the threaded shaft 286. The parts of the motor support carriage 276 and the parts that they support, such as the transverse rail 280 and threaded shaft 266, move synchronously with movement of the motor support carriage 276 and cause the sample capture cell 138 to travel along the X-axis defined by the threaded shaft 286. It will be appreciated that the cup drive motors 252 and 254 and threaded shafts 266 and 286 may have different resolutions and gear ratios. It will also be appreciated that motor configurations employing rotation about radial axis could alternatively or additionally be employed.

In some embodiments, movement of the motor support carriage 276 along the X-axis may also cause linear movement of the sliding seal piston 250 along the X-axis to extend or shorten the effective length of the outflow segment 244 of the transport conduit 140. The movement of the sliding seal piston 250 through the frame 114 of the specimen chamber 102 reduces or eliminates drag force (that would otherwise be caused by extension or shrinkage of the length of the transport conduit 140 and the associated load) on the stages 126 and 128 supporting the specimen chamber 102.

Moreover, the use of the sliding seal piston 250 also facilitates minimization of leakage from the specimen chamber 102. In some embodiments, pressure in the specimen chamber 102 is designed to leak less than $2.1 \times 10^3$ Pa (0.3 psi) over two minutes when the specimen chamber 102 is pressurized to $4.2 \times 10^3$ Pa (0.6 psi) and sealed.

The second cell-positioning subsystem may also include an auxiliary guide shaft 290 that may be anchored by auxiliary supports 292 or by Z-axis actuators, as previously discussed, and that passes through an aperture of the auxiliary support carriage 278. The auxiliary guide shaft 290 can be threaded or non-threaded.

In some embodiments, a mechanical link 294 couples the auxiliary guide shaft 290 to the X-axis motor 254 to cause rotation of the auxiliary guide shaft 290 as well as rotation of the threaded shaft 286. In some embodiments, the mechanical link 294 couples the auxiliary guide shaft 290 to the threaded shaft 286 such that rotation of the threaded shaft 286 causes a corresponding rotation of the auxiliary guide shaft 290. In some embodiments, the mechanical link 294 is a chain (e.g., a roller chain), track, or other perforated or indented material. In some embodiments, each of the auxiliary guide shaft 290 and the threaded shaft 286 is provided with a sprocket that engages with the mechanical link 294. In some embodiments, the mechanical link 294 is a cable or belt. In some embodiments, each of the auxiliary guide shaft 290 and the threaded shaft 286 is provided with a pulley that engages with the mechanical link 294. In some embodiments, the mechanical link 294 is an assembly of gears.

Figure 4:
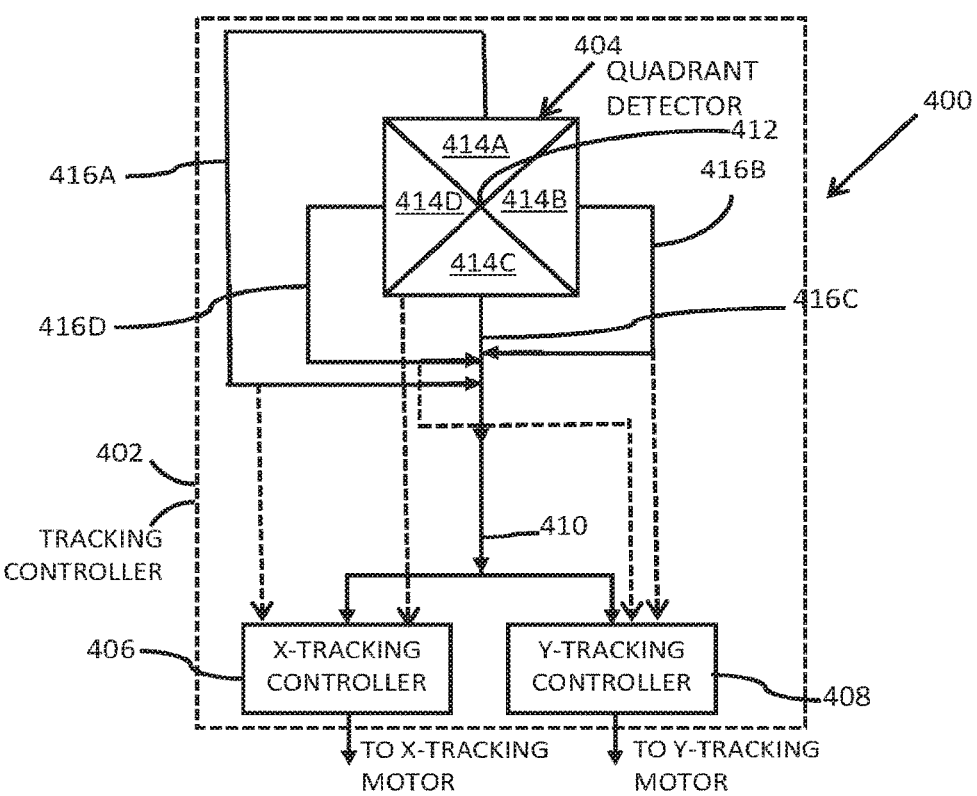
FIG. 4. is a schematic depiction of an alternative exemplary positioning control system for the sampling apparatus of FIG. 1.
Figure 5:
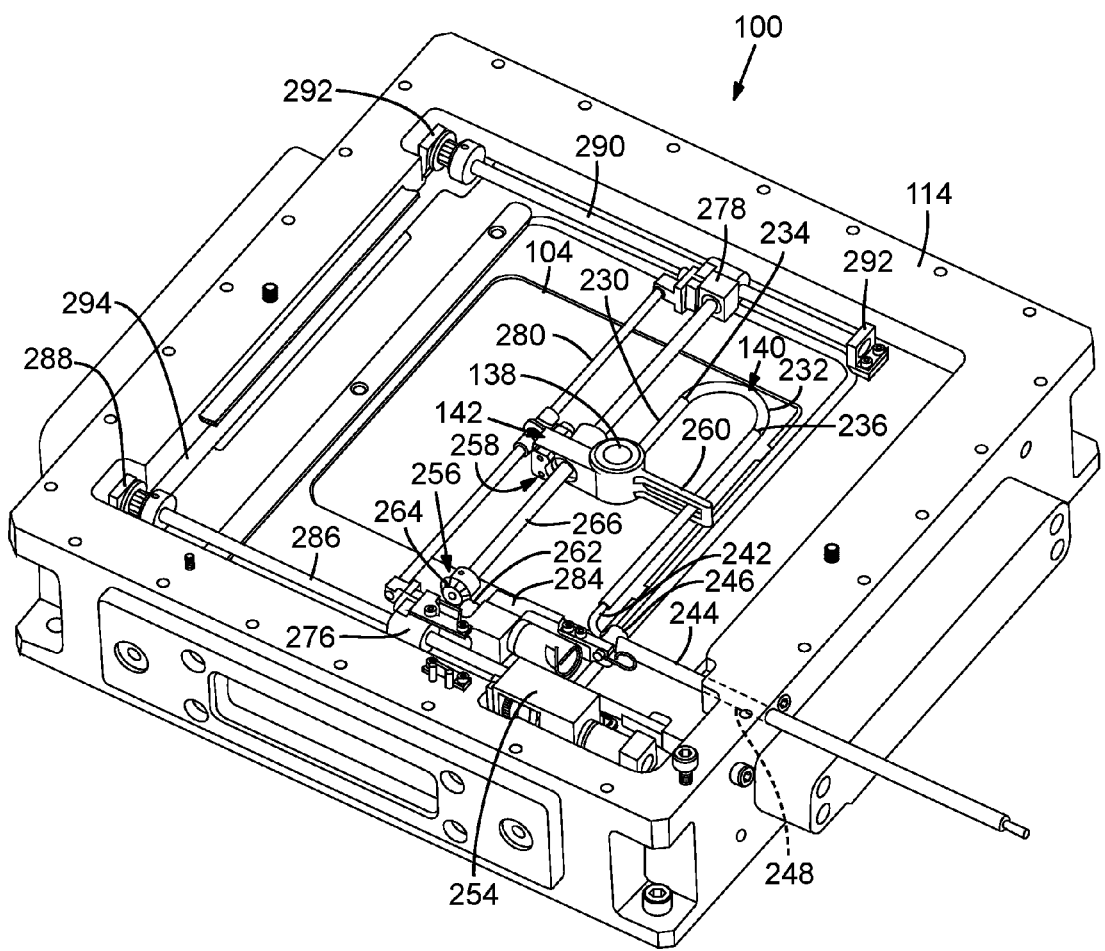
FIG. 5 is an isometric view schematically illustrating another exemplary embodiment of the sampling apparatus of FIG. 1.

In some embodiments, the auxiliary guide shaft 290 is threaded, and the aperture of the auxiliary support carriage 278 may house a ball-bearing assembly (not shown) that acts as a nut about the auxiliary guide shaft 290. The rotation of the auxiliary guide shaft 290 may be synchronized with the motion of the threaded shaft 286 through a mechanical link 294, such as a threaded bridge shaft, by bevel gear assemblies (not shown) or other transverse motion transfer assemblies. Alternatively, and additional X-axis motor (not shown) may cause the auxiliary guide shaft 290 to rotate, and synchronization with the X-axis motor 254 may be imparted by an X-tracking controller 406 (FIG. 4).

Thus, whenever the X-axis motor 254 is caused to turn, it (or an auxiliary X-axis motor) engages the auxiliary guide shaft 290 (possibly through the mechanical link 294) and causes the auxiliary support carriage 278 to move along the threads of the auxiliary guide shaft 290. The parts of the auxiliary support carriage 278 and the parts that they support, such as the transverse rail 280 and threaded shaft 266, move synchronously with movement of the auxiliary support carriage 278 and cause the sample capture cell 138 to travel along the X-axis defined by the auxiliary guide shaft 290.

In some embodiments, one or both of the cell-positioning subsystems may be coupled to one of the stages 126 or 128. In particular, at least one actuator, such as one of the cup drive motors 252 and 254 may be coupled to the specimen stage 126 or 128. Alternatively or additionally, in some embodiments, one or both of the cell-positioning subsystems are coupled to the specimen chamber 102. In some embodiments, one or both of the cell-positioning subsystems may be coupled to the sample capture cell 138 and configured to guide movement of the sample capture cell 138. Alternatively or additionally, in some embodiments, the cell-positioning system could include a robotic arm having the sample capture cell 138 as an end effector. In such embodiments, the robotic arm could be an articulated arm.

With reference again to FIG. 1, the positioning control system 400 may be utilized to track and/or maintain the position of the sample capture cell 138 with respect to a fixed location, such as the location of the optical path 122 of the laser used for specimen ablation, as the stages 126 and 128 move the specimen chamber 102 and the specimen 104 as prescribed by user or program command. The positioning control system 400 may also be utilized to move the sample capture cell 138 independently from the movement of the stages 126 and 128, the specimen chamber 102, and/or the specimen 104, such as to provide a camera with a wide-angle field of view of the specimen 104 without the sample capture cell 138 in the way (such that the sample capture cell 138 is not aligned with the optical path 122 and/or such that the sample capture cell 138 is out of the field of view of the camera). The positioning control system 400 may also be utilized to re-establish the position of the sample capture cell 138 with respect to the optical path 122 (and re-establish the coordinated tracking) after specimen inspection.

In some embodiments, the positioning control system 400 causes the cell-positioning system to synchronously minor motion control of the specimen-positioning system 124, i.e., the X- and Y-cup drive motors 254 and 252 provide movement to the sample capture cell 138 that is exactly opposite to the movement of the X- and Y-stages 126 and 128. This coordination effectively causes the sample capture cell 138 to remain in a stationary position (for example, with respect to the optical path 122) while the X- and Y-stages 126 and 128 move the specimen chamber around it.

In an exemplary embodiment, the stage controller 130 may cause the X- and Y-stage controllers 132 and 134 to generate clockwise (CW) or counterclockwise (CCW) signal pulses for each microstep (or series of microsteps) that the X- and Y-stage controllers 132 and 134 cause the respective the X- and Y-stages 126 and 128 to move. The tracking controller 402, which may include separate X- and Y-tracking controllers 406 and 408, receives the pulses and interprets them into an absolute position of the X- and Y-stages 126 and 128 with respect to a coordinate location of zero, such as the position of the optical path 122, for example. Based on the absolute position, the X- and Y-tracking controllers 406 and 408 can calculate an equivalent position of the sample capture cell 138 for the respective X- and Y-cup drive motors 254 and 252, taking into account different step sizes and different screw-gear ratios.

As position changes to the X- and Y-stages 126 and 128 are implemented by the stage controller 130, the position changes are detected by the tracking controllers 402 and new positions for the X- and Y-cup drive motors 254 and 252 can be determined, wherein the X- and Y-cup drive motors 254 and 252 move the sample capture cell 138 to maintain an absolute position of zero. The X- and Y-tracking controllers 406 and 408 may issue the step and direction commands to driver electronics of the respective X- and Y-cup drive motors 254 and 252. The command signals may propagate from the X- and Y-tracking controllers 406 and 408 (or driver electronics) by wire (or air-sealed circuit board) through the frame 114 and directly to the respective X- and Y-cup drive motors 254 and 252.

In some embodiments, eight wires used to control the X- and Y-cup drive motors 254 and 252 are passed through the frame 114 of the specimen chamber 102 via a sealed bulkhead passthrough. Some embodiments may employ a two-sided connector through the frame 114. In some embodiments, the wire leads are epoxy glued to a plate that gets screwed to the bulkhead opening. In some embodiments, in which the electronics are positioned within the specimen chamber 102, the connection could employ a simple two-wire serial and power or could employ a wireless RF power and RF signal.

FIG. 4 is a schematic depiction of an alternative or additional exemplary positioning control system 400 for the sampling apparatus 100 of FIG. 1, wherein motion and control of the motion of the sample capture cell 138 is independent of the motion and control of the X- and Y-stages 126 and 128. In some embodiments, the positioning control system 400 may employ a tracking controller 402 that includes a quadrant detector 404 (or a position sensitive detector) as well the separate X- and Y-tracking controllers 406 and 408.

An external reference signal 410 can be interpreted by electronics within (or external to) the specimen chamber to drive the X- and Y-cup drive motors 254 and 252 (without input concerning the position of the X- and Y-stages 126 and 128) to maintain alignment with the optical path 122. In some embodiments, the laser beam from the sample generator 108 may be split to form a reference beam 412 that is directed at the quadrant detector 404. The quadrant detector 404 has a defined center where four identical photocells 414A-D meet so that the quadrant detector 404 is most sensitive to beam-position variations near the center. When the quadrant detector 404 receives a reference signal 410 that indicates that the reference beam 412 is off center, the tracking controller 402 through the X- and Y-tracking controllers 406 and 408 can, in a closed-loop manner, issue commands to the X- and Y-cup drive motors 254 and 252 to maintain the position of the sample capture cell 138 to the reference laser beam (and, therefore, to the optical path 122) within the limits of the quadrant detector 404.

In some embodiments, the photocurrent of each photocell 414 may be sent along respective signal paths 416A-D to separate amplifiers (not shown) before being processed with signals from the other photocells 414A-D to generate top-minus-bottom difference and right-minus-left difference signals. A summation signal may also be provided for normalization purposes. The single paths 416A-D may be fed directly to the appropriate X- and Y-tracking controller 406 and 408 as shown in broken lines.

It will be appreciated that the positioning control system 400 may utilize both the mirror control system and the external reference system if desirable.

When the sample capture cell 138 is in a desired position with respect the specimen 104, the sample generator may deploy the laser beam to generate a plume containing particles of the specimen material that can be captured by the sample capture cell 138 and transported via the transport conduit 140 to the sample preparation system 112 and then transferred into the analysis system 110 for compositional analysis.

LA-ICP-MS and LA-ICP-OES techniques for analyzing the specimen material are well known and are commercially available. Exemplary LA-ICP-MS systems include, but are not limited to, Element 2™ sold by Thermo Scientific of Waltham, Mass., 7700x ICP-MS™ sold by Agilent Technologies of Santa Clara, Calif., and AttoM™ sold by Nu Instruments Limited of Wrexham, United Kingdom. Some supplementary configurations for sample preparation systems 112 and analysis systems 110 and/or their connections are to the specimen chamber 102 are disclosed in U.S. Pat. Pub. No. 2014-0227776, which is incorporated herein by reference and which assigned to the assignee of this application.

The foregoing is illustrative of embodiments of the invention and is not to be construed as limiting thereof. Although a few specific example embodiments have been described, those skilled in the art will readily appreciate that many modifications to the disclosed exemplary embodiments, as well as other embodiments, are possible without materially departing from the novel teachings and advantages of the invention.

Accordingly, all such modifications are intended to be included within the scope of the invention as defined in the claims. For example, skilled persons will appreciate that the subject matter of any sentence or paragraph can be combined with subject matter of some or all of the other sentences or paragraphs, except where such combinations are mutually exclusive.

It will be obvious to those having skill in the art that many changes may be made to the details of the above-described embodiments without departing from the underlying principles of the invention. The scope of the present invention should, therefore, be determined by the following claims, with equivalents of the claims to be included therein.

The invention claimed is:

1. An apparatus for handling specimen material removed from a laser ablation site of a specimen, the apparatus comprising:
   a specimen stage configured to support the specimen;
   a specimen-positioning system for imparting motion to the specimen stage to position the specimen for laser ablation;
   a sample capture cell configured to receive specimen material removed from the laser ablation site when the sample capture cell is operably proximate to the laser ablation site;
   a cell-positioning system including at least one actuator for imparting motion to the sample capture cell to move the sample capture cell relative to the specimen stage for positioning the sample capture cell adjacent to the laser ablation site wherein the sample capture cell and the specimen stage are independently moveable;
   a sealed specimen chamber, wherein the specimen stage, the sample capture cell, the laser ablation site, the cell-positioning system, and the actuator are situated within the sealed specimen chamber; and
   a transport conduit coupled to the sample capture cell and providing passage for the removed specimen material outside the sealed specimen chamber.

2. The apparatus of claim 1, wherein the at least one actuator includes one of a mechanical actuator, an electromechanical actuator, or a piezoelectric actuator.

3. The apparatus of claim 1, wherein the at least one actuator includes one of a hydraulic actuator or a pneumatic actuator.

4. The apparatus of claim 1, wherein the at least one actuator includes a magnetic actuator.

5. The apparatus of claim 1, wherein the cell-positioning system is coupled to the specimen stage.

6. The apparatus of claim 1, wherein the at least one actuator is coupled to the specimen stage.

7. The apparatus of claim 1, wherein the cell-positioning system further includes at least one cell stage coupled to the sample capture cell and configured to guide movement of the sample capture cell.

8. The apparatus of claim 7, wherein the at least one cell stage includes a linear stage.

9. The apparatus of claim 7, wherein the at least one cell stage includes a rotary stage.

10. The apparatus of claim 1, wherein the cell-positioning system includes:
    a first cell-positioning subsystem configured to move the sample capture cell relative to the specimen stage along a first direction; and
    a second cell-positioning subsystem configured to move the sample capture cell relative to the specimen stage along a second direction different from the first direction.

11. The apparatus of claim 10, wherein the first cell-positioning subsystem includes:
    a first screw gear coupled to the specimen stage and extending along the first direction;
    a carriage coupled to first screw gear and the sample capture cell; and
    a first motor coupled to the first screw gear, wherein the first motor is configured to rotate the first screw gear, and wherein the carriage is coupled to the first screw gear such that rotation of the first screw gear causes relative linear motion of the carriage along the first direction.

12. The apparatus of claim 11, wherein the first cell-positioning subsystem further includes a first guide coupled to the specimen stage and to the carriage assembly, and wherein the sample capture cell is located between first screw gear and the first guide.

13. The apparatus of claim 12, wherein the first guide is a screw gear.

14. The apparatus of claim 13, further comprising a mechanical link coupling the first guide to the first screw gear such that rotation of the first screw gear causes a corresponding rotation of the first guide.

15. The apparatus of claim 14, wherein the carriage is coupled to the first guide such that rotation of the first guide causes relative linear motion of the carriage assembly along the first direction.

16. The apparatus of claim 10, wherein the second cell-positioning subsystem includes:
    a second screw gear coupled to the carriage assembly and extending along the second direction; and
    a second motor coupled to the second screw gear, wherein the first motor is configured to rotate the first screw gear, and wherein the carriage assembly is coupled to the first screw gear such that rotation of the first screw gear causes relative linear motion of the carriage assembly along the first direction.

17. The apparatus of claim 1, wherein the specimen chamber is sealed against ambient atmosphere such that the specimen chamber leaks less than $2.1 \times 10^3$ Pa (0.3 psi) over two minutes after the specimen chamber is pressurized to $4.2 \times 10^3$ Pa (0.6 psi) and sealed.

18. The apparatus of claim 1, wherein the sample capture cell is moveable relative to the specimen stage and the cell-positioning system is coupled to the sample capture cell.

19. The apparatus of claim 1, further comprising a laser configured to direct laser light into an interior of the specimen chamber along an optical path, wherein the sample capture cell is arranged along the optical path, between the specimen stage and the laser.

* * * * *